United States Patent [19]

Beau

[11] Patent Number: 5,629,453

[45] Date of Patent: May 13, 1997

[54] PROCESS FOR THE MANUFACTURE OF HYDROXYALKOXYBENZOPHENONES

[75] Inventor: Jean-Pierre Beau, Montsoult, France

[73] Assignee: Great Lakes Chemical France, Cergy St. Christophe, France

[21] Appl. No.: 478,902

[22] Filed: Jun. 7, 1995

[30] Foreign Application Priority Data

Jan. 13, 1995 [FR] France .................. 95 00359

[51] Int. Cl.$^6$ ................................. C07C 45/45
[52] U.S. Cl. ........................ 568/322; 568/322
[58] Field of Search .................... 568/322

[56] References Cited

U.S. PATENT DOCUMENTS

| | | | |
|---|---|---|---|
| 3,639,483 | 2/1972 | Shioda et al. | 568/322 |
| 3,769,349 | 10/1973 | Yukntomi et al. | 568/322 |
| 3,843,729 | 10/1974 | Lachmann et al. | 568/372 |
| 4,568,429 | 2/1986 | Liu | 568/322 |
| 4,990,680 | 2/1991 | Neumann et al. | 568/322 |

FOREIGN PATENT DOCUMENTS

| | | | |
|---|---|---|---|
| 795782 | 2/1973 | Belgium | 568/322 |
| 154092 | 12/1984 | European Pat. Off. | 568/322 |
| 2473506 | 1/1980 | France | 568/322 |
| 3904371 | 2/1989 | Germany | 568/322 |
| 37588 | 7/1984 | Hungary | 568/322 |
| 762667 | 3/1977 | South Africa | 568/322 |

OTHER PUBLICATIONS

Zhu et al, Chemical Abstracts, vol. 120, #322,871 (1994).

*Primary Examiner*—James H. Reamer
*Attorney, Agent, or Firm*—Woodard, Emhardt, Naughton Moriarty & McNett

[57] ABSTRACT

The invention relates to a process for the manufacture of hydroxyalkoxybenzophenones of general formula:

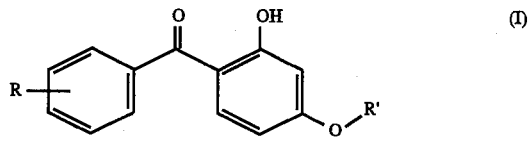

in which
R represents a hydrogen atom, a hydroxyl radical or an optionally substituted $C_1$ to $C_{20}$ alkyl or aralkyl group,
R' represents a hydrogen atom or an optionally substituted $C_1$ to $C_{20}$, preferably $C_1$, $C_8$ or $C_{12}$, alkyl or aralkyl group, by reaction of an α,α,α-trihalotoluene with a polyhydroxyphenol or a hydroxyalkoxyphenol.

According to this process, the reaction is carried out in the presence of a sulphur-containing or selenium-containing catalyst consisting of a compound of the mercaptan or seleno-mercaptan type and preferably containing a short $C_1$ to $C_{20}$, preferably $C_2$ to $C_{12}$, carbon chain which is largely sterically unhindered.

17 Claims, No Drawings

PROCESS FOR THE MANUFACTURE OF HYDROXYALKOXYBENZOPHENONES

The invention relates to a process for the manufacture of hydroxyalkoxybenzophenones of general formula:

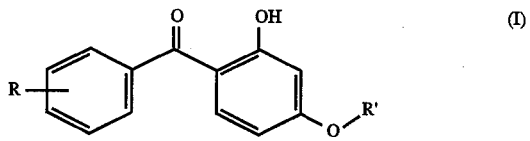

in which
R represents a hydrogen atom, a hydroxyl radical or an optionally substituted $C_1$ to $C_{20}$ alkyl or aralkyl group,
R' represents a hydrogen atom or an optionally substituted $C_1$ to $C_{20}$, preferably $C_1$, $C_8$ or $C_{12}$, alkyl or aralkyl group.

It is known to prepare the hydroxyalkoxybenzophenones of formula (I) by reaction of an $\alpha,\alpha,\alpha$-trihalotoluene with a polyhydroxyphenol or a hydroxyalkoxyphenol in the presence of a specific catalyst.

In this regard,
U.S. Pat. No. 3,769,349 proposes to perform the process in an aqueous-acetic medium,
U.S. Pat. No. 3,639,483 proposes to perform the process in an aqueous-alcoholic medium in the presence of alkyl halide,
patent BE 795,782 proposes to work in two successive steps in different solvents, namely, an aqueous-alcoholic solvent first, followed by a ketonic solvent,
patent FR-A-2,473,506 involves a more or less heavy alcohol in a stoichiometric amount,
patent ZA 7,602,667 priority U.S. Pat. No. 589,967 proposes to work in the presence of dimethylsulphoxide,
patents EP-A-154,092 and U.S. Pat. No. 4,568,429 propose to use N-methylpyrrolidone as catalyst,
patent DE 39 04 371 of 16/08/90 proposes to use alcoholic or polyhydroxylated emulsifying agents or surfactants,
patent HU 37,588 proposes to involve Lewis acids of the type $ZnCl_2$, $MgCl_2$, $AlCl_3$.

The abovementioned known processes have the drawback of using considerable amounts of catalysts and/or of co-solvent; moreover, they are complicated and generate very considerable amounts of non-recyclable effluents which it is necessary to destroy at great expense.

Finally, in all these processes, the benzophenones obtained starting with trichlorotoluene, and more particularly 2,4-dihydroxybenzophenone, are contaminated with considerable amounts of xanthenones which constitute coloured impurities, and especially up to approximately 90% by weight with 6-hydroxy-9-phenylfluorone, also referred to as 6-hydroxy-9-phenyl-3H-xanthen-3-one, of formula:

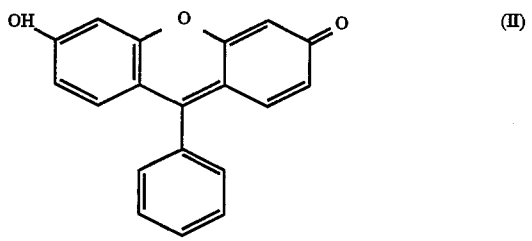

as well as with other similar xanthenic ring systems.

The undesired xanthenones are formed by the action of a second polyhydroxyphenol molecule on the trihalogenated carbon; one of the aims of the invention is to prevent their formation.

The above mentioned solvated impurities constituted by the xanthenones represent a major drawback, since it is extremely difficult to get rid of them subsequently. Moreover, the main product released by the reaction of the trichloromethylbenzene is hydrochloric acid, and it is not possible, with any of the catalysts previously used, to work in a concentrated hydrochloric medium without generating considerable amounts of these highly coloured xanthenones.

Industrially, this therefore leads to the products formed being distilled under very weak vacuums and at very high temperatures, thereby resulting in expensive industrial constraints.

However, the benzophenones of formula (I), and in particular 2,4-dihydroxybenzophenone, have the property of absorbing ultraviolet solar radiation and, in this respect, they are used as anti-UV additives for polymers or in the cosmetics industry.

In view of these industrial uses, the user consequently wishes to have available benzophenones of the greatest possible purity and of the least possible coloration.

The objective of the invention is thus, above all, to provide a process which not only no longer has the drawbacks of the prior processes but which, in addition, leads to hydroxyalkoxybenzophenones which are virtually free of coloured impurities.

As a result of extensive research, the Applicant Company has had the merit of finding that this objective was achieved when, in the processes of the type in question, use is made of a sulphur-containing or selenium-containing catalysts consisting of a mercaptan or of a seleno-mercaptan acting as a nucleophile in a very acidic medium, this being all the more unexpected since sulphur-containing products other than mercaptans do not give satisfactory results.

It follows that the process for the preparation of the hydroxyalkoxybenzophenones of formula (I) in accordance with the invention, in which an $\alpha,\alpha,\alpha$-trihalotoluene is reacted with a polyhydroxyphenol or a hydroxyalkoxyphenol, is characterized in that the reaction is carried out in the presence of a sulphur-containing or selenium-containing catalyst consisting of a compound of the mercaptan or seleno-mercaptan type and preferably containing a short $C_1$ to $C_{20}$, preferably $C_2$ to $C_{12}$, carbon chain which is largely sterically unhindered.

It is possible, although the Applicant Company does not wish to be bound by this theory, that the catalyst used in accordance with the invention adds itself temporarily to the product formed as an intermediate during the reaction of the $\alpha,\alpha,\alpha$-trihalotoluene (preferably trichlorotoluene) with the polyhydroxyphenol (for example resorcinol).

By virtue of this process, the action of a second molecule of polyhydroxyphenol would then be slowed down, or even completely prevented, thereby avoiding the final formation of the xanthenones.

The simplified reaction diagram representing this process might be as follows:

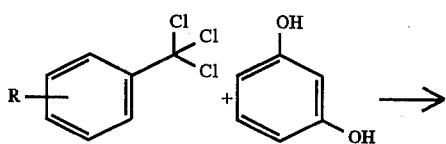

-continued

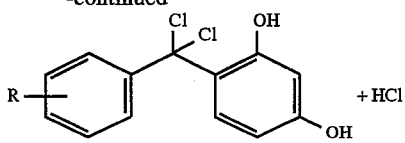
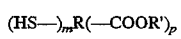
+HCl

The abovementioned non-isolable intermediate would then rearrange, again losing HCl acid, leading to the following probable product (III):

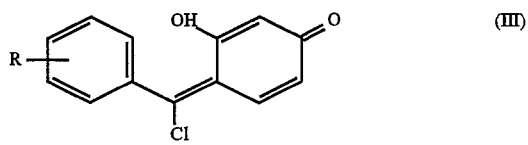
(III)

The intermediate (III) would in turn form, with the catalyst used in accordance with the invention, a very temporary addition compound of the type.

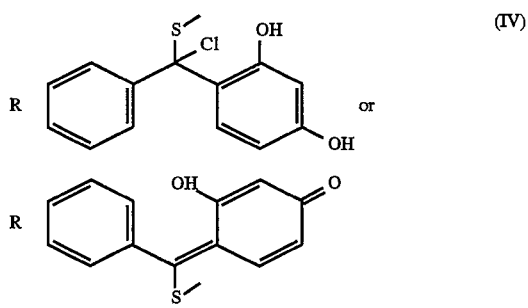
(IV)

or in which S represents the nucleophilic atom of the catalyst group.

The sulphur atom is replaced by a selenium atom when the catalyst used is a seleno-mercaptan.

The temporary addition of the catalyst limits the attack of a second molecule of resorcinol on the compound (III), by virtue of the formation of a compound of type (IV).

The latter compound leads, on acidic hydrolysis, to the corresponding benzophenone (I), the hydrolysis releasing the catalyst.

One of the advantages of the process according to the present invention is to reduce the amounts of xanthenones formed secondarily during the synthesis to a very low level, the hydroxyalkoxybenzophenones obtained having a xanthenone content which is especially less than 0.5% by weight.

These yields of pure isolated product, in this instance 2,4-dihydroxybenzophenone, are excellent, of the order of 95 to 99% relative to the two main constituents, and are thus considerably superior to those described in the prior art.

According to an advantageous embodiment of the process in accordance with the invention, the compound of mercaptan type is of the formula R(—SH)$_n$ (v)

in which R represents a hydrogen atom or an optionally substituted $C_1$ to $C_{30}$, preferably $C_2$ or $C_3$, alkyl, cycloalkyl or aralkyl group, n being an integer equal to 1 or 2.

According to an advantageous embodiment of the process in accordance with the invention, the catalyst used is represented by the above mentioned formula (V) in which n is greater than 2 and may take a value tending towards infinity, the catalysts in question then being in the form of a resin or a polymer.

According to another advantageous embodiment of the process in accordance with the invention, the catalyst used and consisting of a compound of mercaptan type is an acid-mercaptan of formula (HS—)$_m$R(—COOR')$_p$ (VI)

in which

R represents an optionally substituted $C_1$ to $C_{30}$, preferably $C_2$ or $C_3$, alkyl, cycloalkyl or aralkyl group, and R' represents a hydrogen atom, an optionally substituted $C_1$ to $C_{20}$ alkyl, cycloalkyl or aralkyl group or a metal atom, preferably an alkali metal or alkaline-earth metal atom, m and p, which are identical to or different from each other, are integers from 1 to 5.

According to another embodiment or the process in accordance with the invention, the catalyst of formula (V) or (VI) is chosen from the group comprising:

lauryl mercaptan, n-hexyl mercaptan, cyclohexyl mercaptan, 1,2-ethanedithiol, 1,6-hexanedithiol, mercaptoacetic (thioglycolic) acid, 3-mercaptopropionic acid, thiolactic (2-mercaptopropionic) acid, mercaptosuccinic acid (thiomalic acid), thiosalicylic acid (mercaptobenzoic acid), mercaptonicotinic acid and mercaptopyruvic acid as well as the corresponding eaters and salts.

According to another advantageous embodiment of the process in accordance with the invention, the catalyst used and consisting of a compound of mercaptan type is a mercaptosulphonic acid of formula

HS—R—SO$_3$R' (VII)

in which R and R' have the meanings given in relation to the formula (VI).

Among the preferred compounds of formula (VII) are mercaptoethanesulphonic acid and 1-mercaptopropanesulphonic acid as well as the alkali metal salts, especially the sodium salt, thereof.

According to another advantageous embodiment of the process in accordance with the invention, the reaction is carried out in the presence of a sulphur-containing compound, which is introduced before the trihalo derivative is run in, and which is capable of giving a compound of the mercaptan type by prior reaction with the acidic reaction medium, the said reaction possibly being:

of the "hydrolysis" type, the sulphur-containing compound then being chosen from the group comprising thioacetals and hemithioacetals, thiolactones such as γ-thiobutyrolactone, dimers, ortho esters and products of self-esterification of the acid-thiols corresponding to the formula (VI) and in particular those of thioglycolic acid, trithiocarbonates such as vinylene trithiocarbonate and ethylene trithiocarbonate, dithiocarboxylic acids, dithiophosphoric acids and dithiophosphinic acids, or of the "decomposition" type, the sulphur-containing compound then being chosen from the group comprising thioacids, thioamides such as thiourea, thioacetamide, thioacetanilide, thiobenzamide, thiouracil, thiosemicarbazide and thiophosgene, or of the "reduction" type with the secondary involvement of a reducing agent, the sulphur containing compound then being chosen from the group comprising organic (cyclo)-di- or polysulphides and metal di- or polysulphides.

According to another embodiment of the process in accordance with the invention, the reaction is carried out in the presence of an amount of catalyst from 0.1 mol % to 100 mol %, preferably from 5 to 10 mol %, relative to the $\alpha,\alpha,\alpha$-trihalotoluene, the slight gain obtained beyond this limit not justifying the use of greater amounts.

According to another embodiment of the process in accordance with the invention, the reaction is carried out in a solvent comprising an acidic aqueous phase which is concentrated and, preferably, saturated with hydrochloric acid, this is a considerable simplification.

By virtue of the purity of the hydroxyalkoxybenzophenones prepared using the process according to the invention, the distillation treatments necessary in the case of the products obtained by the processes of the prior art are eliminated.

In other terms, the hydroxyalkoxybenzophenones obtained in accordance with the invention are pure enough to be employed as they are in the synthesis of the alkylated derivatives used as UV stabilizers in the polymer and cosmetics industries.

As a result of the presence of the mercaptan-type catalyst, it is possible to perform the process in a concentrated, or even saturated (at the saturation corresponding to the temperature at which the reaction is carried out) hydrosolvated state without degrading the xanthenones in question.

The aqueous hydrochloric medium may consequently be recycled, which constitutes a considerable advantage since the amount of effluents needing to be destroyed is decreased, or even eliminated altogether; it follows therefrom that the process according to the invention is particularly economical.

Furthermore, by recycling the hydrochloric aqueous phase and by readjusting the amount of catalyst, hydroxyalkoxybenzophenones of increasing purity, that is to say of increasingly lower optical density, are obtained.

Finally, on account of the presence of the catalyst, the amount of aqueous phase used during the process in accordance with the invention may be greatly reduced in comparison with the amounts necessary in the processes of the prior art, which required large volumes of water; the production efficiency of the process according to the present invention is thus much greater than that of the known processes.

For economic reasons, it is preferred to work as closely as possible to stoichiometric conditions, a very slight excess of trihalide nevertheless being desirable; the presence of secondary products, which would risk accumulating in the course of the recyclings if the differences were large, is thus limited.

The temperature at which the process is carried out is controlled to be between 0° and 100° C., preferably between 20° and 40° C., which makes it possible to limit the premature hydrolysis of the trihalo derivative and the lowering of yield which would result.

A subsequent gradual increase of the temperature up to a value of 95° to 100° C. makes it possible to complete the reaction without rushing the gradual precipitation of the benzophenone.

A recrystallization may then be performed if a purer product than that produced by simple draining and washing of the reaction mass is desired. To do this, the crystalline mass is taken up in known solvents for benzophenone, under hot conditions, and washes are performed with water while hot, followed by a crystallization.

Since the main drawback of the mercaptans is their very strong, repulsive odour which is detrimental as far as the process is concerned, it is desirable to increase their molar mass in order to limit these odour problems. In this regard, the mercaptans constituting the preferred catalysts in the sense of the invention are those which contain a hydroxylated or carboxylated polar radical, which limits the vapour pressure of the product and, in the case of the carboxyl and sulfonic group, the odour.

The presence of this polar radical furthermore gives the mercaptan better solubility in the aqueous phase, which is very advantageous.

Conversely, the presence of a radical which is too hydrophilic, such as the $NH_3Cl$ and $NR_2,HCl$ group, makes the mercaptan which bears it totally ineffective from the point of view of its catalysing power.

According to an advantageous embodiment of the process in accordance with the invention, 2,4-dihydroxy-benzophenone is prepared in a first step and is subjected without isolation, in a second step, to methylation using methyl sulphate, which leads to 2-hydroxy-4-methoxybenzo-phenone.

According to an advantageous embodiment of the process in accordance with the invention, 2,4-dihydroxy-benzophenone is prepared in a first step and is subjected without isolation, in a second step, to octylation using actyl chloride, which leads to 2 hydroxy 4 acetyoxy benzo phenone.

In order to assess the effectiveness of a given mercaptan as a catalyst, the optical density of a solution of the benzophenone obtained may be measured.

Indeed, the optical density is closely linked to the degree of contamination of the benzophenone by the xanthenones.

This measurement of the optical density is made by application of the Beer-Lambert law, at the benzophenone maximum absorption, with the dilutions and the methods usually used by those skilled in the art. In the case of 2,4-dihydroxybenzophenone, the measurement is made at 450 nm, the dry benzophenone being dissolved to an amount of 10% in acetone, the cell having a thickness of 4 cm.

The invention may be better understood with the aid of the non-limiting examples which follow and which relate to advantageous embodiments of the process in accordance with the invention, to comparisons between the catalysts of the prior art and those used in accordance with the invention, to comparisons between various sulphur-containing compounds showing the superiority of those used in accordance with the invention, to the determination of the influence of the amount of catalyst used, and to the influence on the optical density of the benzophenone obtained from the recycling of the hydrochloric aqueous phase.

EXAMPLE 1

Preparation of 2,4-dihydroxybenzophenone 110 g of resorcinol, 750 g of water, 7.5 g of 32% HCl and 2.5 g of lauryl mercaptan are mixed together. 200 g (1.00 mol) of $\alpha, \alpha, \alpha$ trichlorotaluene are run into this mixture over 5 hours, at a temperature of 35° to 40° C.

The temperature is then maintained at 60° C. for 2 hours.

The orange-yellow crystalline mass obtained is drained on a sinter funnel at 50° C.

This product is washed three times with 100 ml of water.

It is dried in a ventilated oven at 80° C. and 205 g of crude 2,4-dihydroxybenzophenone, equivalent to a 95.8% yield, are obtained as a product having a melting point of 139°–143° C. and an optical density of 490 (10% solution in acetone at 450 nm), which corresponds to a total xanthenone content of 0.5%.

EXAMPLE 2

Preparation of 2,4-dihydroxybenzophenone 110 g of resorcinol, 600 ml of 32% HCl and 10 g of mercaptoethanol are mixed together.

200 g (1.02 mol) of α, α, α-trichlorotoluene are run in over 3 hours, at a temperature of 35° to 40° C.

The temperature is then maintained at 70°–80° C. for 1 hour.

The orange-yellow crystalline mass obtained is drained on a sinter funnel and is washed three times with 100 ml of water.

The product is dried in a ventilated oven at 80° C. and 210 g of crude 2,4-dihydroxybenzophenone, equivalent to a 98% yield, are obtained as a product having a melting point of 139°–143° C. and an optical density of 220 (10% solution in acetone at 450 nm), which corresponds to a total xanthenone content of 0.35%.

EXAMPLE 3

Preparation of 2,4-dihydroxybenzophenone 110 g of resorcinol, 700 ml of 37% of HCl and 15 g of thioglycolic acid (2-mercaptoacetic acid) are mixed together.

200 g (1.02 mol) of α, α, α-trichlorotoluene are run in over 3 hours, at a temperature of 50° C.

The temperature is then gradually raised to 95° C.

The crystalline mass may then be drained or taken up in a good water-immiscible solvent, followed by washes of the organic phase according to the usual practices of those skilled in the art.

After recrystallization, followed by draining and drying in a ventilated oven, 207 g of 2,4-dihydroxybenzophenone, equivalent to a 96.5% yield, are obtained as a product having a melting point of 139°–143° C. and an optical density of 500 (10% solution in acetone at 450 nm, 4 cm cell), which corresponds to a total xanthenone content of approximately 0.5%.

EXAMPLE 4

The procedure is performed in the same way as for example 3, but the catalyst is made of 10 g of methylthioglycolic ester (formula VI). After work up, 169 g of 2,4-dihydroxy-benzophenone are obtained, equivalent to a 79% yield, having an optical density of 420.

EXAMPLE 5

The procedure is performed in the same way as for example 3, but the catalyst is made of 15 g of buthylmercaptopropionic ester (formula VI). After work up, 194 g of 3,4-dihydroxybenzophenone are obtained, equivalent to a 90.7% yield, having an optical density of 120.

EXAMPLE 6

This example shows that in order to obtain low coloured benzophenones, it is not absolutely essential to perform the synthesis at high temperature, provided a catalyst is used in accordance with the invention.

110 g of resorcinol, 600 g of 32% HCl and 12 g of 3-mercepto-1-propanesulfonic acid sodium salt (formula VII) are mixed together. 200 g (1.03 mol) of α, α, α trichlorotoluene are run into the mixture over 3 hours, at a temperature of 30° C. This same temperature is then maintained for 3 hours more, while stirring, the product is then filtered off, washed with water, dried in a ventilated oven. 205 g or 2,4-dihydroxybenzophenone, equivalent to a 96% yield, are obtained as a product having a melting point of 139°–143° C. and an optical density of 100 to 140, which correspond to a total xanthenon content of 0.4 to 0.6%.

EXAMPLE 7

Preparation of 3,4 dihydroxybenzophenone and of 3-hydroxy 4-methoxybenzophenone 110 g of resorcinol, 560 ml of 32% HCl and 10 g of 3 mercoptopropionic acid are mixed together.

200 g (1.02 mol) of α, α, α-trichlorotoluene are run in over 3 hours, at a temperature of 35° to 40° C.

The temperature is then maintained at 70°–80° C. for 1 hour.

600 g of solvent are run in to dissolve the crystalline mass and the temperature in the mass is brought to 95° C.

The lower acidic aqueous phase is separated out after setting or the phases has taken place, and this acidio phase may be recycled.

The organic phase is washed with 150 ml of water containing 30 g of sodium hydrogen carbonate, and then with 100 ml of water.

The organic phase containing dihydroxybenzophenone is dried azeotropically.

If it is desired to obtain 2-hydroxy-4-methoxybenzophenone, the methylation may be performed directly by salification using $K_2CO_3$ and methyl sulphate without isolating the intermediate benzophenone.

190 g of 2-hydroxy-4-methoxybenzophenone are obtained, having a melting point of 62.5°–63.8° C. and an optical density of 0.9 (20% solution of dry benzophenone, measurement at 450 nm in a 1 cm cell).

If a higher purity is sought, the dihydroxybenzophenone may be recrystallized beforehand by cooling.

The dark yellow crystalline mass is then drained on a sinter funnel at 20° C. and is washed with 100 g of the same solvent.

The product is dried in a ventilated oven at 80° C. and 205 g of purified 2,4-dihydroxybenzophenone, corresponding to a yield of 95.8%, are obtained as a product having a melting point of 139°–144° C. and an optical density of 80–120 (10% solution in acetone at 450 nm), the total xanthenone content consequently being from 0.20 to 0.25%.

EXAMPLE 8

This example shows that the way of getting the chemicals reacted is not very important, provided a catalyst is used in accordance with the invention. The procedure is performed with the same materials and same general process as for example 7, but the run of reactants is reversed: a mixture of 110 g of resorcine and 560 g of 32% HCl are fed in two hours on a mixture of 200 g α,α,α-trichlorotoluene and 10 g of mercaptopropionic acid, at a temperature of 50° C. The following procedure is then exactly performed as in example 7. It is also possible to combine this with the synthesis of 2-hydroxy-4-methoxybenzophenone as already mentioned in example 7, or to perform the alkylation with octyl chloride after the salification is being obtained with $K_2CO_3$ in a similar manner, without the intermediate benzophenone to be isolated. If not, 192 g of 2,4-dihydroxybenzophenone are obtained after work up, having an optical density of 50, which corresponds to a total xanthenon content of less than 0.2%.

EXAMPLE 9

Preparation of 2,4-dihydroxybenzophenone and of 2-hydroxy-4-methoxybenzophenone

The lower aqueous phase isolated in Example 7 (or acidic mother liquors) is taken up and 110 g of resorcinol are added, along with 5 g of 3-mercaptopropionic acid, then the α,α,α-trichlorotoluene is run in, the procedure being performed exactly as in Example 7.

208 g of 2,4-dihydroxybenzophenone, corresponding to a yield of 97%, are obtained as a product having an optical density of 50 to 60 (10% solution in acetone at 450 nm), the total xanthenone content consequently being from 0.15 to 0.20%.

It is also possible, in the same manner as in Example 7, to combine this with the synthesis of 2-hydroxy-4-methoxybenzophenone by taking the crystalline mass up beforehand in a solvent, followed by performing washings, salification and then the methylation with methyl sulphate. 188 g of 2-hydroxy-4-methoxybenzophenone are then obtained, having a melting point of 62.5° to 63.8° C. and an optical density of 0.5 to 1.

EXAMPLE 10

Preparation of 2-hydroxy-4-methoxybenzophenone 124 g of 3-methoxyphenol, 600 ml of 32% HCl and 10 g of 3 mercaptopropionic acid are mixed together.

200 g (1.02 mol) of α,α,α-trichlorotoluene are run in over 3 hours, at a temperature between 35° and 40° C.

The temperature is then maintained at 70°–80° C. for 1 hour.

The lower acidic aqueous phase is separated out after settling of the phases has taken place.

The organic phase is washed with 150 ml of water containing 30 g of sodium hydrogen carbonate, and then with 100 ml of water.

200 ml of a low-molecular-weight alcohol are run in and the mixture is cooled in order to crystallize the 2-hydroxy-4-methoxybenzophenone.

The product is filtered off and is then washed with a minimum of this same alcohol.

It is dried in a ventilated oven at 50° C. and 114 g of purified 2-hydroxy-4-methoxybenzophenone, corresponding to a yield of 50%, are obtained as a product having an optical density of 2 (20% solution in acetone, measurement at 450 nm) and a melting point of 62.5°–63.8° C.

EXAMPLE 11

Preparation of 2-hydroxy-4-octyloxybenzophenone 222 g of 3-octoxyphenol, 600 ml of 32% HCl and 10 g of 3-mercaptopropionic acid are mixed together.

200 g (1.02 mol) of α,α,α-trichlorotoluene are run in over 3 hours, at a temperature of 35° to 40° C.

The temperature is then maintained at 70°–80° C. for 1 hour.

The lower acidic aqueous phase is separated out after settling of the phases has taken place.

The organic phase is washed with 150 ml of water containing 30 g of sodium hydrogen carbonate, and then with 100 ml of water.

200 ml of lower alcohol are run in and the mixture is cooled to crystallize the 2-hydroxy-4-methoxybenzophenone.

The product is filtered off and washed with a minimum of the same lower alcohol.

It is dried in a ventilated oven at 40° C. and 146 g of 2-hydroxy-4-octyloxybenzophenone, corresponding to a yield of 45%, are obtained as a product having a melting point of 47°–59° C. and an optical density of 0.25.

EXAMPLE 12

This example shows the superiority of the catalysts used in accordance with the invention relative to nucleophilic compounds which may theoretically serve as catalysts and relative to catalysts used according to the prior art.

To do this, 20 samples of 2,4-dihydroxybenzophenone were prepared using a proportion of 2 to 10 mol % of the following catalysts:

TABLE I

| Sample No. | Nature of the catalyst used | Optical density |
|---|---|---|
| 1 | Methanesulphonic acid | ~10 800 |
| 2 | 1,4-thioxane | ~10 000 |
| 3 | NONE | ~7 000 |
| 4 | carbon disulfide | ~7 200 |
| 5 | Phenol | ~6 500 |
| 6 | dimethylamino pyridine hydrochloride | ~6 500 |
| 7 | Triflic acid | ~6 000 |
| 8 | 2-Mercaptoethylamine hydrochloride | ~5 600 |
| 9 | Methyldialkyl($C_{18}$)amine | ~5 000 |
| 10 | sodium dioctyl-sulphosuccinate | ~4 800 |
| 11 | dimethylstilfoxide | ~4 000 |
| 12 | Polyvinyl alcohol | ~4 000 |
| 13 | 1-Morcaptotrimethoxysilane | ~3 000 |
| 14 | n-Hexanol | 1 700 |
| 15 | Lauryl mercaptan | 1 500 |
| 16 | Thioglycolic acid | 500 |
| 17 | 2-Mercaptoethanol | 220 |
| 18 | 3-Mercaptopropionic acid | 150 |
| 19 | 3-mercapto-1-propanesulfonic acid, sodium salt | 100–140 |
| 20 | butyl-3-mercaptopropionate | 100–120 |

The results collected in Table I show that the samples prepared in accordance with the invention exhibit a very significant enhancement in the optical density and thus in the quality of the product.

EXAMPLE 13

In this example, the influence of the amount of catalyst used is studied.

Six samples of 2,4-dihydroxybenzophenone were prepared using increasing amounts of catalyst consisting of 3-mercoptopropionio acid, namely.

| Sample No. | Amount of 3-mercaptopropionic acid per mole of trichlorotoluene |
| --- | --- |
| 1 | 2.5 g |
| 2 | 5 g |
| 3 | 10 g |
| 4 | 20 g |
| 5 | 30 g |
| 6 | 200 g |

Measurement of the optical density for the six samples under the conditions indicated above gives the following results:

| Sample No. | Optical density |
| --- | --- |
| 1 | 2 500 |
| 2 | 300 |
| 3 | 100 |
| 4 | 80 |
| 5 | 80 |
| 6 | 55 |

It follows therefrom that, from an economic point of view, there is no point in exceeding 10 g of catalyst per mole of α,α,α-trihalotoluene.

EXAMPLE 14

The influence of recycling the hydrochloric aqueous phase was studied.

To do this, five samples of 2,4-dihydroxybenzophenone were prepared successively by working as indicated in Example 4 for the first sample and by recycling the hydrochloric aqueous phase for the preparation of each of the samples 2 to 5, while at the same time readjusting the amount of catalyst.

Measurement of the optical density on each of the five samples gives the following results:

| Sample No. | Optical density |
| --- | --- |
| 1 | 120 |
| 2 | 70 |
| 3 | 60 |
| 4 | 55 |
| 5 | 40 |

The advantage derived by recycling the hydrochloric aqueous phase is clearly apparent.

I claim:

1. A process for the manufacture of hydroxyalkoxybenzophenones of general formula:

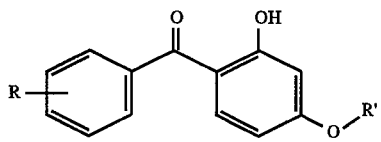 (I)

in which R represents a hydrogen atom, a hydroxyl radical or a $C_1$ to $C_{20}$ alkyl or aralkyl group, and R' represents a hydrogen atom or a $C_1$ to $C_{20}$ alkyl or aralkyl group, by reaction of an α,α,α-trihalotoluene with a polyhydroxyphenol or a hydroxyalkoxyphenol, characterized in that the reaction is carried out in the presence of a sulphur-containing or selenium-containing catalyst consisting of a compound of the mercaptan or seleno-mercaptan type.

2. The process of claim 1 in which R' represents a hydrogen atom or a $C_1$, $C_8$ or $C_{12}$ alkyl or aralkyl group.

3. The process of claim 1 in which the reaction is carried out in the presence of a sulphur-containing or selenium-containing catalyst consisting of a compound of the mercaptan or seleno-mercaptan type and containing a $C_1$ to $C_{20}$ carbon chain which is largely sterically unhindered.

4. The process of claim 3 in which the reaction is carried out in the presence of a sulphur-containing or selenium-containing catalyst consisting of a compound of the mercaptan or seleno-mercaptan type and containing a $C_2$ to $C_{12}$ carbon chain which is largely sterically unhindered.

5. The process according to claim 1, characterized in that the reaction is carried out in the presence of a compound of mercaptan type of the formula:

$$R_1(-SH)_n \quad (V)$$

in which $R_1$ represents a hydrogen atom or a $C_1$ to $C_{30}$ alkyl, cycloalkyl or aralkyl group, and n is an integer equal to 1 or 2.

6. The process according to claim 5 in which $R_1$ represents a hydrogen atom or a $C_2$ or $C_3$ alkyl, cycloalkyl or aralkyl group.

7. The process according to claim 1, characterized in that the reaction is carried out in the presence of a compound of acid-mercaptan type of formula $$(HS-)_m R_2(-COOR_3)_p \quad (VI)$$

in which $R_2$ represents a $C_1$ to $C_{30}$ alkylene, cycloalkylene or aralkylene group, and $R_3$ represents a hydrogen atom, a $C_1$ to $C_{20}$ alkyl, cycloalkyl or aralkyl group or metal atom, and m and p, which are identical to or different from each other, are integers from 1 to 5.

8. The process according to claim 7, characterized in that $R_2$ represents a $C_2$ or $C_3$ alkylene, cycloalkylene or aralkylene group.

9. The process according to claim 7, characterized in that $R_3$ represents a hydrogen atom, a $C_1$ to $C_{20}$ alkyl, cycloalkyl or aralkyl group or an alkali metal or alkaline-earth metal atom.

10. The process according to claim 1, characterized in that the reaction is carried out in the presence of a catalyst selected from the group consisting of lauryl mercaptan, n-hexyl mercaptan, cyclohexyl mercaptan, 1,2-ethanedithiol, 1,6-hexanedithiol, mercaptoacetic (thioglycolic) acid, 3-mercaptopropionic acid, thiolactic (2-mercaptopropionic) acid, mercaptosuccinic acid (thiomalic acid), thiosalicylic acid (mercaptobenzoic acid), mercaptonicotinic acid and mercaptopyruvic acid, and their esters and salts.

11. The process according to claim 1, characterized in that the reaction is carried out in the presence of a mercaptosulphonic acid of formula $$HS-R_2-SO_3R_3 \quad (VII)$$

in which $R_2$ represents a hydrogen atom, or a $C_1$ to $C_{20}$ alkylene, cycloalkylene or aralkylene group, and $R_3$ represents a hydrogen atom, a $C_1$ to $C_{20}$ alkyl, cycloalkyl or aralkyl group or a metal atom.

12. The process according to claim 11, characterized in that $R_3$ represents a hydrogen atom, a $C_1$ to $C_{20}$ alkyl, cycloalkyl or aralkyl group or an alkali metal or alkaline-earth metal atom.

13. The process according to claim 1, characterized in that the reaction is carried out in the presence of an amount of catalyst from 0.1 mol % to 100 mol % relative to the α,α,α-trihalotoluene.

14. The process according to claim 13, characterized in that the reaction is carried out in the presence of an amount of catalyst from 5 mol % to 10 mol % relative to the α,α,α-trihalotoluene.

15. The process according to claim 1, characterized in that the reaction is carried out in a solvent consisting of a concentrated acidic aqueous phase.

16. The process according to claim 15, characterized in that the reaction is carried out in a solvent consisting of a concentrated acidic aqueous phase saturated with hydrochloric acid.

17. The process according to claim 16, characterized in that the acidic aqueous solvent is recycled after recovery of the hydroxyalkoxybenzophenone formed.

* * * * *

UNITED STATES PATENT AND TRADEMARK OFFICE
CERTIFICATE OF CORRECTION

PATENT NO. : 5,629,453
DATED : May 13, 1997
INVENTOR(S) : Jean-Pierre Beau

It is certified that error appears in the above-indentified patent and that said Letters Patent is hereby corrected as shown below:

In col. 2, line 31, please change "catalysts" to --catalyst--.

In col. 6, line 1, please delete "phenone".

In col. 6, line 63, please change "trichlorotaluene" to --trichlorotoluene--.

In col. 8, line 10, please change "or" to --of--.

In col. 8, line 29, please change "setting" to --settling-- and change "acidio" to --acidic--.

In col. 10, Table I, Sample No. 6, please change "pyridtne" to --pyridine--.

In col. 10, Table I, Sample No. 11, please change "dimethylstilfoxide" to --dimethylsulfoxide--.

In col. 10, Table I, Sample No. 13, please change "1-" to --y--.

In col. 10, line 67, please change "mercoptopropionio" to --mercaptopropionic--.

Signed and Sealed this

Twenty-third Day of September, 1997

Attest:

BRUCE LEHMAN

Attesting Officer

Commissioner of Patents and Trademarks